US012662435B2

(12) United States Patent
Yoshitoku et al.

(10) Patent No.: US 12,662,435 B2
(45) Date of Patent: Jun. 23, 2026

(54) OLEFIN PRODUCTION DEVICE AND OLEFIN PRODUCTION METHOD

(71) Applicants: MITSUBISHI HEAVY INDUSTRIES, LTD., Tokyo (JP); The University of Tokyo, Tokyo (JP)

(72) Inventors: Koichiro Yoshitoku, Tokyo (JP); Yukio Tanaka, Tokyo (JP); Atsuhiro Yukumoto, Tokyo (JP); Noriaki Senba, Tokyo (JP); Kazuhiro Takanabe, Tokyo (JP)

(73) Assignees: MITSUBISHI HEAVY INDUSTRIES, LTD., Tokyo (JP); The University of Tokyo, Tokyo (JP)

( * ) Notice: Subject to any disclaimer, the term of this patent is extended or adjusted under 35 U.S.C. 154(b) by 344 days.

(21) Appl. No.: 18/280,265

(22) PCT Filed: Mar. 2, 2022

(86) PCT No.: PCT/JP2022/008917
§ 371 (c)(1),
(2) Date: Sep. 4, 2023

(87) PCT Pub. No.: WO2022/191000
PCT Pub. Date: Sep. 15, 2022

(65) Prior Publication Data
US 2024/0067587 A1      Feb. 29, 2024

(30) Foreign Application Priority Data
Mar. 8, 2021    (JP) ................................. 2021-036462

(51) Int. Cl.
*C07C 2/84*          (2006.01)
*B01J 8/04*          (2006.01)
(Continued)

(52) U.S. Cl.
CPC ............... *C07C 2/84* (2013.01); *B01J 8/0492* (2013.01); *B01J 8/0496* (2013.01); *B01J 21/08* (2013.01);
(Continued)

(58) Field of Classification Search
CPC ......... C07C 2/84; C07C 2/82; C07C 2523/04; C07C 2523/10; C07C 2523/30;
(Continued)

(56) References Cited

U.S. PATENT DOCUMENTS

2014/0107385 A1* 4/2014 Schammel ............... B01J 8/001
                                                               585/501
2018/0353940 A1* 12/2018 Liang ..................... B01J 23/002

FOREIGN PATENT DOCUMENTS

CN        1356172 A      7/2002
CN        1356173 A      7/2002
(Continued)

OTHER PUBLICATIONS

International Preliminary Report on Patentability and Written Opinion issued in corresponding International Application No. PCT/JP2022/008917, dated Sep. 21, 2023, with English translation (10 pages).
(Continued)

*Primary Examiner* — Ali Z Fadhel
(74) *Attorney, Agent, or Firm* — Osha Bergman Watanabe & Burton LLP

(57)          ABSTRACT

An olefin production device for producing an olefin from a raw material gas containing methane and oxygen includes a reactor containing: a first catalyst; and a second catalyst disposed downstream of the first catalyst in a flow direction of the raw material gas. The first catalyst is a catalyst in which a zirconium salt or carbonate of an alkali metal, an oxide of an alkaline earth metal, an oxide of one kind of
(Continued)

10a lanthanoid element, a composite oxide containing a lanthanoid element, or a combination thereof is supported on a support. The second catalyst is a catalyst containing a tungsten oxide, phosphate, or carbonate of an alkali metal.

5 Claims, 4 Drawing Sheets

(51) Int. Cl.

| | | |
|---|---|---|
| *B01J 21/08* | (2006.01) |
| *B01J 23/10* | (2006.01) |
| *B01J 23/30* | (2006.01) |
| *B01J 27/232* | (2006.01) |
| *C07C 2/82* | (2006.01) |

(52) U.S. Cl.
CPC .............. *B01J 23/10* (2013.01); *B01J 23/30* (2013.01); *B01J 27/232* (2013.01); *C07C 2/82* (2013.01); *B01J 2208/025* (2013.01); *C07C 2523/04* (2013.01); *C07C 2523/10* (2013.01); *C07C 2523/30* (2013.01); *C07C 2527/167* (2013.01)

(58) Field of Classification Search
CPC ........ C07C 2527/167; C07C 2527/232; C07C 2521/08; C07C 61/00; B01J 8/0492; B01J 8/0496; B01J 21/08; B01J 23/10; B01J 23/30; B01J 27/232; B01J 2208/025; B01J 23/002; B01J 23/34; Y02P 20/52
See application file for complete search history.

(56) References Cited

FOREIGN PATENT DOCUMENTS

| | | | |
|---|---|---|---|
| CN | 109438159 | A | 3/2019 |
| CN | 112439400 | A | 3/2021 |
| JP | 2011032257 | A | 2/2011 |
| JP | 6308998 | B2 | 4/2018 |
| JP | 2019167265 | A | 10/2019 |
| JP | 2019202945 | A | 11/2019 |
| JP | 2020-028821 | A | 2/2020 |
| WO | 2013177461 | A2 | 11/2013 |
| WO | 2015106023 | A1 | 7/2015 |

OTHER PUBLICATIONS

International Search Report and Written Opinion issued in corresponding International Application No. PCT/JP2022/008917, dated May 24, 2022 (8 pages).

* cited by examiner

OLEFIN PRODUCTION DEVICE AND OLEFIN PRODUCTION METHOD

TECHNICAL FIELD

The present disclosure relates to an olefin production device and an olefin production method.

The present application claims priority based on Japanese Patent Application No. 2021-036462 filed on Mar. 8, 2021, the entire content of which is incorporated herein by reference.

BACKGROUND ART

As described in Patent Document 1, it is well known that olefins such as ethylene are produced by oxidative coupling of methane (OCM) reaction.

CITATION LIST

Patent Literature

Patent Document 1: JP6308998B

SUMMARY

Problems to be Solved

Catalysts for the OCM reaction include a low temperature catalyst, which is active at low temperatures below 700° C., and a high coupling selectivity catalyst, which provides high coupling selectivity, and they have different reaction mechanisms. When the former catalyst is used, the reaction is possible at low temperatures, but there is a risk that the coupling selectivity may decrease at high temperatures, while when the latter catalyst is used, high coupling selectivity is achieved, but the reaction requires high temperatures.

In view of the above problem, an object of at least one embodiment of the present disclosure is to provide an olefin production device and an olefin production method whereby it is possible to achieve high methane conversion and high coupling selectivity.

Solution to the Problems

To achieve the above object, an olefin production device according to the present disclosure is an olefin production device for producing an olefin from a raw material gas containing methane and oxygen, the olefin production device comprising a reactor containing: a first catalyst; and a second catalyst disposed downstream of the first catalyst in a flow direction of the raw material gas. The first catalyst is a catalyst in which a zirconium salt or carbonate of an alkali metal, an oxide of an alkaline earth metal, an oxide of one kind of lanthanoid element, a composite oxide containing a lanthanoid element, or a combination thereof is supported on a support. The second catalyst is a catalyst containing a tungsten oxide, phosphate, or carbonate of an alkali metal.

Further, an olefin production method according to the present disclosure is an olefin production method for producing an olefin from a raw material gas containing methane and oxygen, comprising: a first reaction step of producing an olefin from methane in the raw material gas by oxidative coupling reaction using a first catalyst; and a second reaction step of producing an olefin from methane in the raw material gas that has undergone the first reaction step by oxidative coupling reaction using a second catalyst. The first catalyst is a catalyst in which a zirconium salt or carbonate of an alkali metal, an oxide of an alkaline earth metal, an oxide of one kind of lanthanoid element, a composite oxide containing a lanthanoid element, or a combination thereof is supported on a support. The second catalyst is a catalyst containing a tungsten oxide, phosphate, or carbonate of an alkali metal.

Advantageous Effects

With the olefin production device and the olefin production method of the present disclosure, since the reaction heat from the methane oxidative coupling reaction using the first catalyst is used to obtain the temperature required for the methane oxidative coupling reaction using the second catalyst, high methane conversion and high coupling selectivity can be achieved by controlling the outlet temperature of the first catalyst and supplying the gas that has passed through the first catalyst to the second catalyst.

DETAILED DESCRIPTION

Hereinafter, an olefin production device and an olefin production method according to embodiments of the present disclosure will be described based on the drawings. The embodiments each indicate one aspect of the present disclosure, do not intend to limit the present disclosure, and can optionally be modified within a range of a technical idea of the present disclosure.

<Configuration of Olefin Production Device According to Embodiment of Present Disclosure>

Figure 1:
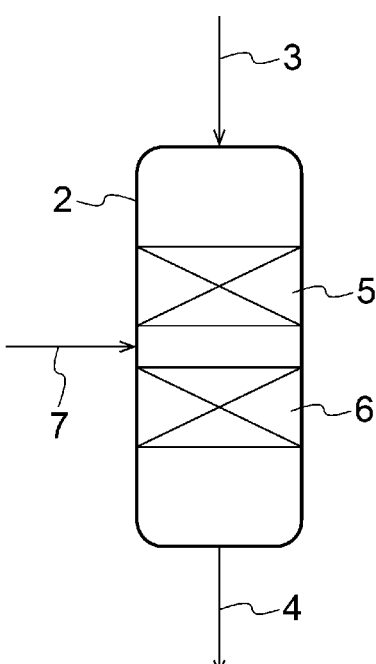
FIG. 1 is a schematic configuration diagram of an olefin production device according to an embodiment of the present disclosure.

As shown in FIG. 1, an olefin production device 1 according to an embodiment of the present disclosure includes a reactor 2. To the reactor 2 is connected a raw material gas supply line 3 for supplying a raw material gas containing methane and oxygen into the reactor 2 and a discharge line 4 for discharging the gas in the reactor 2 from the reactor 2. The reactor 2 contains a first catalyst 5 and a second catalyst 6 disposed downstream of the first catalyst 5 in the flow direction of the raw material gas. The olefin production device 1 may also be provided with an oxygen supply line 7 connected to the reactor 2 for supplying oxygen into the reactor 2 between the first catalyst 5 and the second catalyst 6, although it is not an essential configuration.

<Configuration of Modification of Olefin Production Device According to Embodiment of Present Disclosure>

Figure 2:
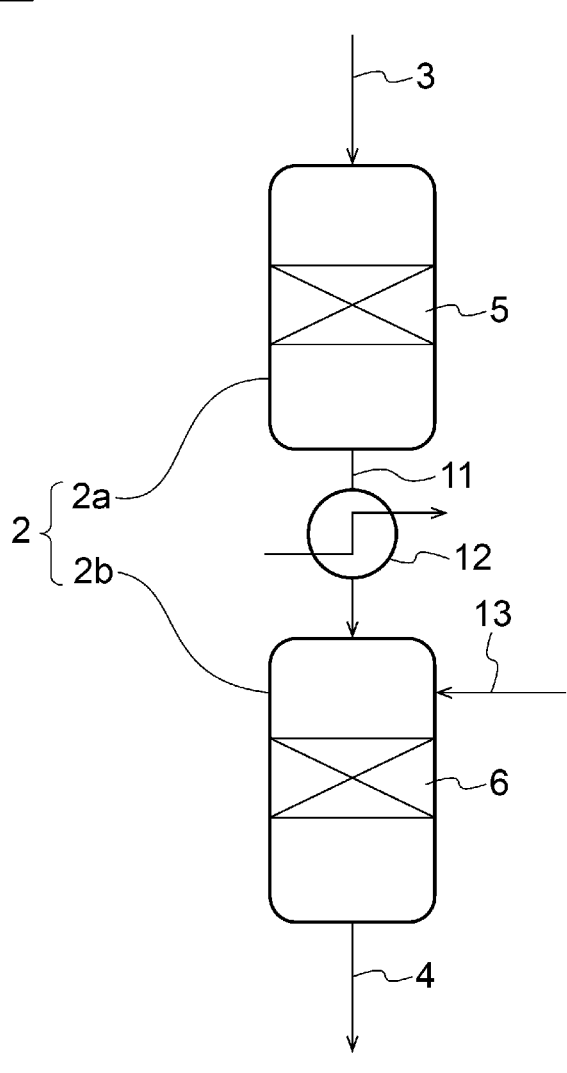
FIG. 2 is a schematic configuration diagram of a modification of an olefin production device according to an embodiment of the present disclosure.

As shown in FIG. 2, the reactor 2 of another olefin production device 10 according to an embodiment of the present disclosure includes a first reactor 2a to which the raw material gas supply line 3 is connected and a second reactor 2b to which the discharge line 4 is connected. The first reactor 2a and the second reactor 2b are connected through a connection line 11. The first reactor 2a contains a first catalyst 5, and the second reactor 2b contains a second catalyst 6. The olefin production device 10 may also be provided with a cooler 12 disposed on the connection line 11 for cooling the gas flowing out of the first reactor 2a, and an oxygen supply line 13 connected to the second reactor 2b for supplying oxygen into the second reactor 2b upstream of the second catalyst 6, although they are not essential configurations. Further, such as an olefin production device 10a shown in FIG. 3, the olefin production device 10 shown in FIG. 2 may be modified such that the second reactor 2b contains the first catalyst 5 and the second catalyst 6 downstream of the first catalyst 5, and at least one of the oxygen supply line 13 or an oxygen supply line 14 for supplying oxygen into the second reactor 2b between the first catalyst 5 and the second catalyst 6 is connected to the second reactor 2b.

<Catalyst Used in Olefin Production Device According to Embodiment of Present Disclosure>

The first catalyst 5 is a catalyst in which a zirconium salt or carbonate of an alkali metal such as Li, Na, or K, an oxide of an alkaline earth metal such as Ca, Sr, or Ba, an oxide of one kind of lanthanoid element such as La, Ce, Pr, or Tb, a composite oxide containing a lanthanoid element such as La—Ce, or a combination thereof is supported on a support. Examples of the catalytic component supported on the support include, but are not limited to, $La_2O_3$, $CeO_2$, $CaO$, $SrO$, $BaO$, $Pr_2O_3$, $Tb_2O_3$, $Na_2ZrO_3$, $Li_2ZrO_3$, and $K_2ZrO_3$. Examples of the support include, but are not limited to, oxides including at least one of $ZnO$, $CeO_2$, $Cr_2O_3$, $MnO_2$, $Fe_2O_3$, $Fe_3O_4$, $TiO_2$, $ZrO_2$, $Al_2O_3$, $La_2O_3$, $CaO$, $SrO$, $MgO$, or $SiO_2$.

The second catalyst 6 is a catalyst containing a tungsten oxide, phosphate, or carbonate of an alkali metal such as Li, Na, or K. Examples of the catalytic component include, but are not limited to, $Na_2WO_4$, $K_2WO_4$, $Li_2WO_4$, $Na_3PO_4$, $Li_3PO_4$, $K_3PO_4$, or those doped with at least one of metal species such as Mn or Sn. The second catalyst 6 may be configured not to support any of these catalytic components that can exist in solid form on the support. When the catalytic component is supported on the support, the entire surface of the support is preferably coated with the catalytic component so that the surface of the support is not exposed. For the second catalyst 6, as with the first catalyst 5, any support can be used.

<Operation of Olefin Production Device According to Embodiment of Present Disclosure (Olefin Production Method)>

Next, an operation of the olefin production device according to an embodiment of the present disclosure will be described. As shown in FIG. 1, the raw material gas flowing through the raw material gas supply line 3 is supplied to the reactor 2. In the reactor 2, first, under the catalytic action of the first catalyst 5, ethylene is produced by the reaction represented by the following reaction equation (1).

$$2CH_4 + O_2 \rightarrow C_2H_4 + 2H_2O \qquad (1)$$

The catalytic reaction mechanism of the first catalyst 5 is as follows. First, oxygen is adsorbed on the active component of the first catalyst 5 to become reactive oxygen species ($O^*$). Methane reacts with the reactive oxygen species $O^*$ and abstracts hydrogen atoms therefrom to produce intermediate methyl radicals. The methyl radicals react with each other to produce ethane, which undergoes a dehydrogenation reaction to produce ethylene. Such catalytic action of the first catalyst 5 functions with sufficient activity even at low temperatures below 700° C.

In the reactor 2, the raw material gas that has passed through the first catalyst 5 flows into the second catalyst 6. Since the reaction equation (1) is an exothermic reaction, the raw material gas with a temperature of 700° C. or higher due to the reaction heat flows into the second catalyst 6. If the temperature is 700° C. or higher, the second catalyst 6 shows sufficient activity.

The catalytic reaction mechanism of the second catalyst 6 is as follows. The second catalyst 6 produces hydroxyl radicals from water and oxygen. The produced hydroxyl radicals activate methane as methyl radicals, and ethane is produced by coupling of the methyl radicals, and ethylene is produced from ethane by a dehydrogenation reaction. This reaction mechanism has a higher coupling selectivity than the catalytic reaction mechanism of the first catalyst 5.

Thus, since the reaction heat from the methane oxidative coupling reaction using the first catalyst 5 is used to obtain the temperature required for the methane oxidative coupling reaction using the second catalyst 6, high methane conversion and high coupling selectivity can be achieved by controlling the outlet temperature of the first catalyst 5 and supplying the gas that has passed through the first catalyst 5 to the second catalyst 6. The definitions of methane conversion and coupling selectivity will be described later.

As described above, the reaction between methyl radicals produces not only ethane but also C3 or higher alkanes such as propane and butane. This can produce olefins such as propylene and butene in addition to ethylene. Therefore, it can be understood that in reality, not only reactions in which ethylene is produced as in the reaction equation (1), but also reactions in which olefins other than ethylene are produced are occurring.

<Operation of Modification of Olefin Production Device According to Embodiment of Present Disclosure>

Figure 3:
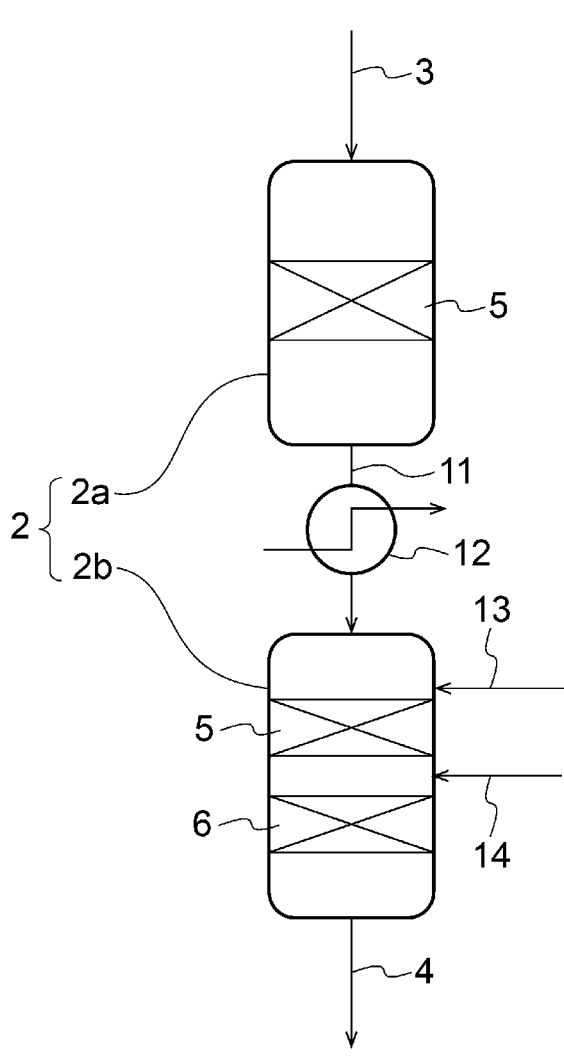
FIG. 3 is a schematic configuration diagram of another modification of an olefin production device according to an embodiment of the present disclosure.

The operations of the olefin production device 10 shown in FIG. 2 and the olefin production device 10a shown in FIG. 3 differ from the operation of the olefin production device 1 in that after the reaction equation (1) occurs due to the catalytic action of the first catalyst 5, the reaction gas flows out of the first reactor 2a and into the second reactor 2b through the connection line 11, where the reaction due to the catalytic action of the second catalyst 6 occurs. The other configurations, especially the respective catalytic reaction mechanisms of the first catalyst 5 and the second catalyst 6, are the same.

If the cooler 12 is provided on the connection line 11, the gas flowing out of the first reactor 2a is cooled by the cooler 12 and flows into the second reactor 2b. The temperature of the gas flowing out of the first reactor 2a is determined by the balance between the amount of gas and the reaction heat. If the temperature is too high, the material of the reactor becomes expensive and the structure becomes complicated, so the temperature in the second reactor 2b is preferably in the range of 700° C. to 900° C.

If the cooler 12 is provided, when the temperature in the second reactor 2b is too high due to the reaction heat in the first reactor 2a, the gas flowing out of the first reactor 2a can be cooled by the cooler 12. Thus, the temperature in the second reactor 2b can be adjusted to an appropriate temperature for the methane oxidative coupling reaction using the second catalyst 6. To adjust the temperature, a sensor may be provided to measure at least one of the temperature in the first reactor 2a or the temperature in the second reactor 2b, and the cooling capacity of the cooler 12 may be controlled based on measurements by the sensor. Further, by supplying additional oxygen to the second reactor 2b via the oxygen supply line 13, 14, the methane conversion can also be improved.
(Examination of Effect of Olefin Production Device and Olefin Production Method of Present Disclosure)

Explanation of Experiments 1 and 2

Figure 4:
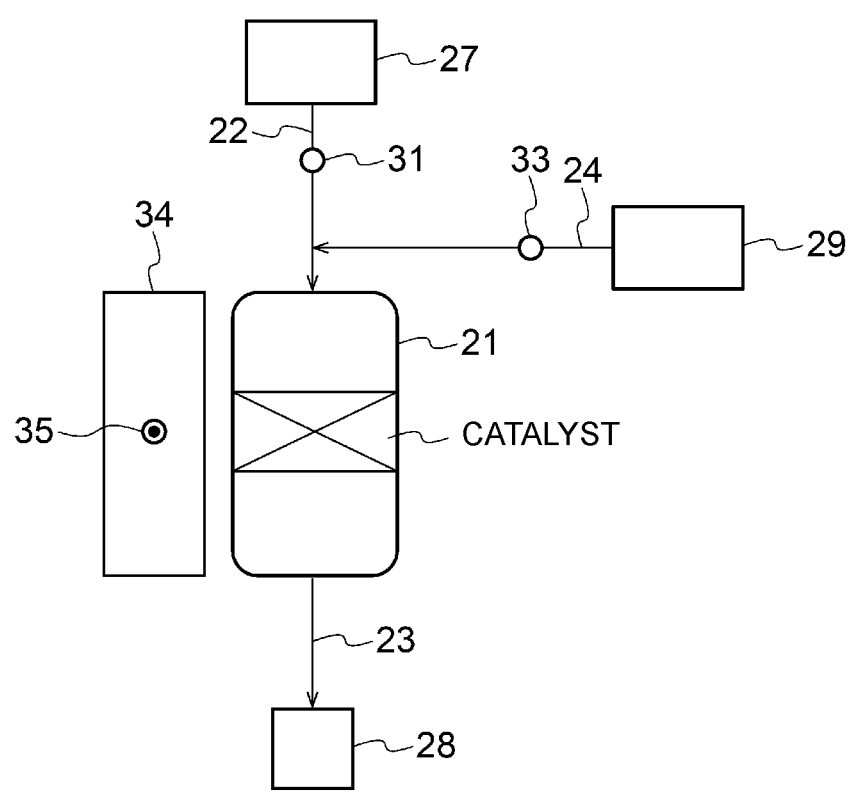
FIG. 4 is a schematic configuration diagram of an experimental apparatus for Experiments 1 and 2.

FIG. 4 shows a schematic configuration of an experimental apparatus 20 for Experiments 1 and 2. The experimental apparatus 20 is equipped with a cylindrical reactor 21. A quartz tube with an inner diameter of 4.5 mm and a length of 200 mm was used as the reactor 21. A supply line 22 connected at one end to a tank 27 for storing methane gas is connected at the other end to one end of the reactor 21 in the axial direction. A discharge line 23 connected at one end to a gas chromatography 28 is connected at the other end to the other end of the reactor 21 in the axial direction. An oxygen supply line 24 connected at one end to an oxygen cylinder 29 is connected to the supply line 22. The oxygen supply line 24 is provided with a flow meter 33 for measuring the flow rate of oxygen flowing through the oxygen supply line 24. The supply line 22 is provided with a flow meter 31 for measuring the flow rate of methane gas flowing through the supply line 22 upstream of the connection position with the oxygen supply line 24. The reactor 21 is heated by an electric furnace 34, and the electric furnace 34 is capable of controlling the heating temperature based on a temperature controller 35.

As Experiment 1, La$_2$CO$_3$/CeO$_2$ (catalytic component/support), corresponding to the first catalyst 5 (see FIGS. 1 and 2), was contained in the reactor 21, while as Experiment 2, Na$_2$WO$_4$/SiO$_2$ (catalytic component/support), corresponding to the second catalyst 6 (see FIGS. 1 and 2), was contained in the reactor 21. Table 1 below shows the experimental conditions (temperature and flow rate settings) for Experiments 1 and 2.

TABLE 1

|  |  | Experiment 1 | Experiment 2 |
|---|---|---|---|
| Catalyst (g) | La$_2$CO$_3$/CeO$_2$ | 0.01 | — |
|  | Na$_2$WO$_4$/SiO$_2$ | — | 0.97 |
| Temperature (° C.) | Temperature controller 35 | 650 | 800 |
| Pressure (MPaA) | Inside of reactor 21 | 0.1 | 0.1 |
| Flow rate (Ncc/min) | Flow meter 31 | 120 | 120 |
|  | Flow meter 33 | 20 | 20 |

The methane conversion and coupling selectivity obtained in Experiments 1 and 2 are shown in Table 2 below.

TABLE 2

|  | Experiment 1 | Experiment 2 |
|---|---|---|
| Methane conversion (%) | 19.5 | 2.8 |
| Coupling selectivity (%) | 71.0 | 76.5 |

Here, the methane conversion and coupling selectivity are defined as follows.

(Expression 1)

$$\text{Methane conversion} = \frac{\text{Reactor inlet methane flow rate} - \text{Reactor outlet methane flow rate}}{\text{Reactor inlet methane flow rate}} \times 100$$

-continued (Expression 2)

$$\text{Coupling selectivity} = \frac{\text{Methane equivalent } C2+ \text{ Compound flow rate}}{\text{Reactor inlet methane flow rate} - \text{Reactor outlet methane flow rate}} \times 100$$

The unit of each flow rate in the above equations is the volume-based flow rate (e.g., Ncc/min), and the "methane equivalent C2+ compound flow rate" in the definition of coupling selectivity means the flow rate converted to methane by dividing the flow rate of each hydrocarbon compound with two or more carbon atoms such as ethane, ethylene, propane, and propylene by the respective carbon number.

Simulation from Results of Experiments 1 and 2

We simulated the following situation: 0.01 g of La$_2$O$_3$/CeO$_2$ catalyst is placed upstream in the reactor 21, and 0.97 g of Na$_2$WO$_4$/SiO$_2$ catalyst is placed downstream thereof. The temperature of the upstream catalyst layer is controlled at 650° C., the temperature of the downstream catalyst layer is controlled at 800° C., and oxygen is supplied between the upstream catalyst layer and the downstream catalyst layer. The expected methane conversion and coupling selectivity were calculated using the results of Experiments 1 and 2. The simulation results are shown in Table 3 below.

TABLE 3

| Catalyst (g) | La$_2$CO$_3$/CeO$_2$ |  | 0.01 |
|---|---|---|---|
|  | Na$_2$WO$_4$/SiO$_2$ |  | 0.97 |
| Pressure (MPaA) |  | 0.1 MPa |  |

TABLE 3-continued

| Flow rate (Ncc/min) | Methane at reactor inlet | 120 |
|---|---|---|
|  | Oxygen at reactor inlet | 20 |
|  | Oxygen added to inlet of Na$_2$WO$_4$/SiO$_2$ catalyst | 16.1 |
|  | Methane conversion (%) | 21.8 |
|  | Coupling selectivity (%) | 71.4 |

Considering that the methane conversion at the outlet of the La$_2$O$_3$/CeO$_2$ catalyst layer is 19.5% in Experiment 1 in Table 2, after passing through the upstream La$_2$O$_3$/CeO$_2$ catalyst layer, 96.6 Ncc/min of unreacted methane should be fed to the downstream Na$_2$WO$_4$/SiO$_2$ catalyst layer. When oxygen is added at a flow rate of 16.1 Ncc/min to the inlet of the downstream Na$_2$WO$_4$/SiO$_2$ catalyst layer to achieve the methane/oxygen ratio in Experiment 2, since a methane conversion of 2.8% is expected according to Table 2, the flow rate of methane at the outlet of the downstream Na$_2$WO$_4$/SiO$_2$ catalyst layer should be 93.9 Ncc/min. Overall, the flow rate of methane is 120 Ncc/min at the inlet of the reactor 21 and 93.9 Ncc/min at the outlet of the reactor 21, which indicates that the methane conversion is 21.8%.

Next, the coupling selectivity is calculated. According to Experiment 1, the coupling selectivity is 71.0% at the outlet of the La$_2$O$_3$/CeO$_2$ catalyst layer, so the coupling product flow rate by the La$_2$O$_3$/CeO$_2$ catalyst is 16.6 Ncc/min in terms of methane, which is the product of the methane flow rate at the inlet of the reactor 21 of 120 Ncc/min, the methane conversion of 19.5%, and the coupling selectivity of 71.0%. Similarly, according to Experiment 2, the coupling selectivity is 76.5% at the outlet of the Na$_2$WO$_4$/SiO$_2$ catalyst layer, so the coupling product flow rate by the Na$_2$WO$_4$/SiO$_2$ catalyst is 2.1 Ncc/min in terms of methane, which is the product of the methane flow rate at the inlet of the Na$_2$WO$_4$/SiO$_2$ catalyst layer of 96.6 Ncc/min, the methane conversion of 2.8%, and the coupling selectivity of 76.5%. Since the overall methane conversion is 21.8%, the converted methane flow rate is 26.2 Ncc/min, which is the methane flow rate of 120 Ncc/min at the inlet of the reactor 21 multiplied by the methane conversion of 21.8%. Therefore, the overall coupling selectivity of the reactor 21 is 71.4%, which is the coupling product flow rate of 18.7 Ncc/min divided by the converted methane flow rate of 26.2 Ncc/min.

The results shown in Tables 2 and 3 indicate that both the methane conversion and coupling selectivity are higher in the simulation results using the first catalyst 5 and the second catalyst 6 than in Experiment 1 using only the first catalyst 5. Compared to Experiment 2 using only the second catalyst 6, the simulation results show a significantly larger methane conversion, although the coupling selectivity is slightly lower. From these results, it can be said that the OCM reaction using both the first catalyst 5 and the second catalyst 6 is superior to the OCM reaction using either the first catalyst 5 or the second catalyst 6 in terms of the balance of methane conversion and coupling selectivity. Further, the coupling selectivity can be improved by using a catalyst containing a tungsten oxide, phosphate, or carbonate of an alkali metal doped with at least one of metal species such as Mn or Sn as the second catalyst 6.

The contents described in the above embodiments would be understood as follows, for instance.

[1] An olefin production device according to one aspect is an olefin production device for producing an olefin from a raw material gas containing methane and oxygen, the olefin production device (1/10) comprising a reactor (2) containing: a first catalyst (5); and a second catalyst (6) disposed downstream of the first catalyst (5) in a flow direction of the raw material gas. The first catalyst (5) is a catalyst in which a zirconium salt or carbonate of an alkali metal, an oxide of an alkaline earth metal, an oxide of one kind of lanthanoid element, a composite oxide containing a lanthanoid element, or a combination thereof is supported on a support. The second catalyst (6) is a catalyst containing a tungsten oxide, phosphate, or carbonate of an alkali metal.

With the olefin production device of the present disclosure, since the reaction heat from the methane oxidative coupling reaction using the first catalyst is used to obtain the temperature required for the methane oxidative coupling reaction using the second catalyst, high methane conversion and high coupling selectivity can be achieved by controlling the outlet temperature of the first catalyst and supplying the gas that has passed through the first catalyst to the second catalyst.

[2] An olefin production device according to another aspect is the olefin production device of [1] where the reactor (2) includes: a first reactor (2a) containing the first catalyst (5); and a second reactor (2b) containing the second catalyst (6). The olefin production device (10) comprises a cooler (12) disposed between the first reactor (2a) and the second reactor (2b).

With this configuration, when the temperature in the second reactor is too high due to the reaction heat in the first reactor, the gas flowing out of the first reactor can be cooled by the cooler. Thus, the temperature in the second reactor can be adjusted to an appropriate temperature for the methane oxidative coupling reaction using the second catalyst.

[3] An olefin production device according to another aspect is the olefin production device of [2] where the second reactor (2b) further contains the first catalyst (5) upstream of the second catalyst (6) in the flow direction of the raw material gas. At least one of: an oxygen supply line (13) for supplying oxygen into the second reactor (2b) upstream of the first catalyst (5) contained in the second reactor (2b) in the flow direction of the raw material gas; or an oxygen supply line (14) for supplying oxygen into the second reactor (2b) between the first catalyst (5) contained in the second reactor (2b) and the second catalyst (6) is connected to the second reactor (2b).

With this configuration, since additional oxygen is supplied into the second reactor, it is possible to further improve the methane conversion.

[4] An olefin production device according to yet another aspect is the olefin production device of [2] or [3] where a temperature in the first reactor (2a) is 700° C. or lower, and a temperature in the second reactor (2b) is 700 to 900° C.

With this configuration, when the temperature in the second reactor is too high due to the reaction heat in the first reactor, the temperature in the second reactor can be adjusted to an appropriate temperature for the methane oxidative coupling reaction using the second catalyst.

[5] An olefin production device according to another aspect is the olefin production device of [1] where the first catalyst (5) and the second catalyst (6) are contained in one reactor (2). An oxygen supply line (7) for supplying oxygen into the reactor (2) between the first catalyst (5) and the second catalyst (6) is connected to the reactor (2).

With this configuration, since additional oxygen is supplied into the reactor, it is possible to further improve the methane conversion.

[6] An olefin production device according to yet another aspect is the olefin production device of any one of [1] to [5] where the first catalyst (5) is a La$_2$O$_3$—CeO$_2$ composite catalyst, and the second catalyst (6) is a catalyst in which Na$_2$WO$_4$ is supported on a SiO$_2$ support.

With this configuration, high methane conversion and high coupling selectivity can be achieved by controlling the outlet temperature of the first catalyst and supplying the gas that has passed through the first catalyst to the second catalyst.

[7] An olefin production device according to yet another aspect is the olefin production device of any one of [1] to [6] where the second catalyst (6) is a catalyst containing a tungsten oxide, phosphate, or carbonate of an alkali metal doped with at least one of Mn or Sn.

With this configuration, it is possible to improve the coupling selectivity.

[8] An olefin production method according to one aspect is an olefin production method for producing an olefin from a raw material gas containing methane and oxygen, comprising: a first reaction step of producing an olefin from methane in the raw material gas by oxidative coupling reaction using a first catalyst; and a second reaction step of producing an olefin from methane in the raw material gas that has undergone the first reaction step by oxidative coupling reaction using a second catalyst. The first catalyst is a catalyst in which a zirconium salt or carbonate of an alkali metal, an oxide of an alkaline earth metal, an oxide of one kind of lanthanoid element, a composite oxide containing a lanthanoid element, or a combination thereof is supported on a support. The second catalyst is a catalyst containing a tungsten oxide, phosphate, or carbonate of an alkali metal.

With the olefin production method of the present disclosure, since the reaction heat from the methane oxidative coupling reaction using the first catalyst is used to obtain the temperature required for the methane oxidative coupling reaction using the second catalyst, high methane conversion and high coupling selectivity can be achieved by controlling the outlet temperature of the first catalyst and supplying the gas that has passed through the first catalyst to the second catalyst.

[9] An olefin production method according to another aspect is the olefin production method of [8], where the second catalyst is a catalyst containing a tungsten oxide, phosphate, or carbonate of an alkali metal doped with at least one of Mn or Sn.

With this configuration, it is possible to improve the coupling selectivity.

REFERENCE SIGNS LIST

1 Olefin production device
2 Reactor
2a First reactor
2b Second reactor
5 First catalyst
6 Second catalyst
7 Oxygen supply line
10 Olefin production device
12 Cooler
13 Oxygen supply line
14 Oxygen supply line

The invention claimed is:

1. An olefin production device for producing an olefin from a raw material gas containing methane and oxygen, the olefin production device comprising a reactor containing:

a first catalyst; and a second catalyst disposed downstream of the first catalyst in a flow direction of the raw material gas, wherein the first catalyst is a catalyst in which a zirconium salt or carbonate of an alkali metal, an oxide of an alkaline earth metal, an oxide of one kind of lanthanoid element, a composite oxide containing a lanthanoid element, or a combination thereof is supported on a support, wherein the second catalyst is a catalyst containing a tungsten oxide, phosphate, or carbonate of an alkali metal, the reactor includes a first reactor and a second reactor, the first reactor contains a part of the first catalyst and does not contain the second catalyst, the second reactor contains the second catalyst and the remainder of the first catalyst which is provided upstream of the second catalyst in the flow direction of the raw material gas, and at least one of an oxygen supply line for supplying oxygen into the second reactor upstream of the first catalyst contained in the second reactor in the flow direction of the raw material gas and an oxygen supply line for supplying oxygen into the second reactor between the first catalyst contained in the second reactor and the second catalyst is connected to the second reactor.

2. The olefin production device according to claim 1, wherein a temperature in the first reactor is 700° C. or lower, and a temperature in the second reactor is 700 to 900° C.

3. The olefin production device according to claim 1, wherein the first catalyst and the second catalyst are contained in one reactor, and wherein an oxygen supply line for supplying oxygen into the reactor between the first catalyst and the second catalyst is connected to the reactor.

4. The olefin production device according to claim 1, wherein the first catalyst is a $La_2O_3$—$CeO_2$ composite catalyst, and the second catalyst is a catalyst in which $Na_2WO_4$ is supported on a $SiO_2$ support.

5. The olefin production device according to claim 1, wherein the second catalyst is a catalyst containing a tungsten oxide, phosphate, or carbonate of an alkali metal doped with at least one of Mn or Sn.

* * * * *